United States Patent
Fevola et al.

(10) Patent No.: US 9,974,722 B2
(45) Date of Patent: May 22, 2018

(54) REDUCED-ETHANOL MOUTH RINSE FORMULATIONS

(71) Applicant: Johnson & Johnson Consumer Inc., Skillman, NJ (US)

(72) Inventors: Michael Fevola, Belle Mead, NJ (US); Stephanie Kirby, Pittsburgh, PA (US); Joseph LiBrizzi, Hillsborough, NJ (US); Saroja Narasimhan, Monmouth Junction, NJ (US); Frank Sun, Belle Mead, NJ (US); Daniel Queiroz, Belle Mead, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days. days.

(21) Appl. No.: 15/298,593

(22) Filed: Oct. 20, 2016

(65) Prior Publication Data

US 2018/0110705 A1 Apr. 26, 2018

(51) Int. Cl.
*A61K 8/34* (2006.01)
*A61Q 11/00* (2006.01)
*A61K 8/46* (2006.01)
*A61K 8/86* (2006.01)

(52) U.S. Cl.
CPC .............. *A61K 8/345* (2013.01); *A61K 8/466* (2013.01); *A61K 8/86* (2013.01); *A61Q 11/00* (2013.01); *A61K 2800/33* (2013.01); *A61K 2800/92* (2013.01)

(58) Field of Classification Search
None
See application file for complete search history.

(56) References Cited

U.S. PATENT DOCUMENTS

| | | | |
|---|---|---|---|
| 3,959,458 A | 5/1976 | Agricola et al. | |
| 4,051,234 A | 9/1977 | Gieske et al. | |
| 5,190,747 A | 3/1993 | Sekiguchi et al. | |
| 5,328,682 A | 7/1994 | Pullen et al. | |
| 5,874,068 A | 2/1999 | Engelman et al. | |
| 6,045,813 A | 4/2000 | Ferguson et al. | |
| 6,106,815 A | 8/2000 | Kang et al. | |
| 6,416,745 B1 | 7/2002 | Markowitz et al. | |
| 6,797,683 B2 | 9/2004 | Shana'a et al. | |
| 7,084,104 B2 | 8/2006 | Martin et al. | |
| 7,087,650 B2 | 8/2006 | Lennon | |
| 2004/0047822 A1 | 3/2004 | Zamudo-Tena et al. | |
| 2006/0013778 A1 | 1/2006 | Hodosh | |
| 2007/0190080 A1 | 8/2007 | Friedman | |
| 2011/0123462 A1 | 5/2011 | Mordas et al. | |
| 2012/0003162 A1* | 1/2012 | Mordas ................ A61K 8/34 424/49 |
| 2012/0213717 A1* | 8/2012 | Shah ................ A61K 8/345 424/59 |

FOREIGN PATENT DOCUMENTS

| | | |
|---|---|---|
| EP | 2401999 A2 | 1/2012 |
| WO | WO 94/16674 A1 | 8/1994 |
| WO | WO 96/16633 A1 | 6/1996 |
| WO | WO-2014135650 A1 * | 9/2014 ............... A61K 8/35 |

OTHER PUBLICATIONS

Mintel; Jun. 30, 2015; "Mint & Menthol Mouthwash" XP002776426: Database accession No. 3196217.
Mintel; Jun. 30, 2015; "Mouthwash" XP002776427: Database accession No. 3193941.

* cited by examiner

*Primary Examiner* — Ernst V Arnold
*Assistant Examiner* — Kyung S Chang

(57) ABSTRACT

Provided are oral care compositions comprising one or more polyol solvents having a total Hansen Solubility Parameter (HSP) of from about 23 to 28, one or more non-anionic bioactive agents, and an aqueous phase, wherein the oral care composition is essentially free of alkyl sulfate surfactants, as well as method of using such compositions in the oral cavity.

19 Claims, No Drawings

REDUCED-ETHANOL MOUTH RINSE FORMULATIONS

FIELD OF THE INVENTION

The present invention relates generally to mouth rinses for the prevention and elimination of bad breath as well as for the reduction of oral microorganisms responsible for the development of dental plaque and tooth decay. In particular, the present invention relates to reduced ethanol mouth rinses effective at preventing the above-mentioned problems.

BACKGROUND OF THE INVENTION

Mouth rinse or mouthwash compositions have been used by people for many years for the prevention of bad breath and for the elimination of bacteria and other oral microorganisms that are responsible not only for bad breath but also tooth decay, plaque and gum diseases such as gingivitis and periodontitis. To this end, antiseptic mouthwashes in the past have been designed to clean the oral cavity, provide fresh breath and kill these pathogenic microbes.

A variety of commercially available antiseptic mouth rinses contain ethanol at levels ranging from approximately 20% up to about 30% by volume, based on the total mouthwash volume (hereinafter referred to as "% v/v"). The ethanol is used both as a vehicle and as a solvent in which the active ingredients, and additives such as astringents, fluorides, color additives, flavor oils, and the like, can be dissolved and then dispersed into solution. The ethanol also provides a preservative role for the mouth rinse during storage and use, and enhances the flavor oil organoleptic cues.

However, the use of ethanol in mouth rinses may sometimes be found unacceptable by some mouthwash users due to a perceived feeling of gum "burn" and/or a "dry mouth" sensation. Accordingly applicants have recognized the desire for mouth rinses that contain no, or low amounts of, ethanol while still achieving sufficient solubility of the composition ingredients and ability of the composition to kill the oral microorganisms responsible for bad breath, plaque and gum disease.

SUMMARY OF THE INVENTION

Provided are oral care compositions comprising one or more polyol solvents having a total Hansen Solubility Parameter (HSP) of from about 23 to 28, one or more non-anionic bioactive agents, and an aqueous phase, wherein the oral care composition is essentially free of alkyl sulfate surfactants.

DETAILED DESCRIPTION OF THE INVENTION

The compositions of the present invention can comprise, consist of, or consist essentially of the essential elements and limitations of the invention described herein, as well any of the additional or optional ingredients, components, or limitations described herein.

The term "comprising" (and its grammatical variations) as used herein is used in the inclusive sense of "having" or "including" and not in the exclusive sense of "consisting only of."

The terms "a" and "the" as used herein are understood to encompass the plural as well as the singular.

Unless otherwise indicated, all documents cited are, in relevant part, incorporated herein by reference; the citation of any document is not to be construed as an admission that it is prior art with response to the present invention. Furthermore, all documents incorporated herein by reference in their entirety are only incorporated herein to the extent that they are not inconsistent with this specification.

The reduced alcohol or non-alcohol mouthwash and mouth rinse compositions described herein provide an antimicrobially effective amount of one or more non-ionic bioactive agents towards oral microorganisms responsible for oral malodor and the build-up of plaque and calculus and the resulting tooth and gum diseases that may follow.

The phrase "antimicrobially effective amount" means the concentration or quantity or level of the compound of the present invention that can attain a particular medical end in having toxic activity for oral microorganisms.

The phrase "orally acceptable" means that the carrier is suitable for application to the surfaces of the oral cavity or ingestion by a living organism including, but not limited to, mammals and humans without undue toxicity, incompatibility, instability, allergic response, and the like.

The term "sterile water", as used herein, means sterile water for irrigation/injection U.S.P. The USP designation means that the sterile water for irrigation/injection is the subject of an official monograph in the current (as of the filing date of this application) US Pharmacopeia.

The term "partition coefficient" means the Octanol Water Partition Coefficient ($K_{ow}$). $K_{ow}$ is the ratio of the concentration by weight of an oil or oily component in the octanol phase and the concentration by weight of the oil or oily component in water phase at equilibrium and at a specified temperature for the biphasic octanol and water system. The logarithm of $K_{ow}$ is called the log P. The experimental values used to calculate the $K_{ow}$ are typically measured at a temperature of between 20° C. to 25° C.

Alternatively, the log P values are conveniently calculated by the "C LOG P" program, also available from Daylight CIS. This program also lists experimental log P values when they are available in the Pomona92 database. The "calculated log P" (C log P) is determined by the fragment approach of Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990, incorporated herein by reference). The fragment approach is based on the chemical structure of each oil or oily component, and takes into account the numbers and types of atoms, the atom connectivity, and chemical bonding. The C log P values, which is considered reliable and a widely used estimate for this physicochemical property, can be used instead of the experimental $K_{ow}$ method for measuring log P values. In certain embodiments, a calculated log P is obtained using the Hansen Solubility Parameters in Practice (HSPiP) software 3rd edition (v3.1.20) as authored by Charles M. Hansen, Steven Abbott and Hiroshi Yamamoto and available for online retrieval at "http://www.hansen-solubility.com/index.php?id=16". The software calculates log P values using the Yamamoto Molecular Break (Y-MB) method, which breaks the molecule down into functional groups (i.e. methyl or carbonyl) to estimate the log P value.

The higher the log P of a compound or component (e.g., the non-anionic bioactive agent), the higher the degree of hydrophobicity of the compound or component.

The term "non-anionic" as used herein means that the bioactive agent is free of negatively charged moieties.

The phrase "reduced level" of alcohol means an amount of a $C_2$-$C_4$ monohydric alcohol up to 1.0% v/v (or about 1.0% v/v), optionally, up to 0.5% v/v (or about 0.5% v/v), optionally, up to 0.1% v/v (or about 0.1% v/v) by volume of the total composition. Optionally, the compositions of the present invention are free of $C_2$-$C_4$ monohydric alcohols.

All percentages, parts and ratios of listed ingredients are based on the active weight of the particular ingredient described per volume (for w/v %) or active weight of the particular ingredient described per total weight of the composition for w/w %, and therefore, the active weights do not include carriers or by-products that may be included in commercially available materials, unless otherwise specified.

Polyol Solvents

The compositions of the present invention comprise at least one polyol solvent having a total Hansen Solubility Parameter (HSP) of from about 23 to 28. Criteria for selecting such solvents to use in the preparation of oral care compositions were developed. Solvents were initially screened by calculating their total Hansen Solubility Parameter (HSP). The Hansen parameters divide the total Hildebrand value into three parts a dispersion force (dD), a polar component (dP), and a hydrogen bonding (dH) component. The Hildebrand value is calculated using the relationship between vaporization, van der Waals forces, and solubility. The total HSP is important as solvents that fell into a particular range were found to be good for solubilizing non-anionic bioactive agents without hindering their bioavailability. The Total HSP (d) is broken into dispersion (dD), polar (dP), and hydrogen bonding (dH) forces and is calculated using equation (1):

$$\delta^2 = \delta D^2 + \delta P^2 + \delta H^2$$

where:
  δD is the dispersion component,
  δP is the polarity component, and
  δH is hydrogen boding component.

Table 1 shows the dispersion, polarity, and hydrogen bonding components for various solvents and total HSP calculation for various solvents.

TABLE 1

Dispersion, polarity, and hydrogen bonding components for solvents and total HSP calculation for solvents.

| Solvent | δD | δp | δH | Total HSP |
|---|---|---|---|---|
| 1,3 propanediol | 16.8 | 13.5 | 23.2 | 31.7 |
| propylene glycol | 16.8 | 9.4 | 23.3 | 30.2 |
| 2,3 butanediol | 15.8 | 8.6 | 23.8 | 29.8 |
| 1,4 butanediol | 16.6 | 11 | 20.9 | 28.9 |
| 1,3 butanediol | 16.5 | 8.1 | 20.9 | 27.8 |
| 2 methyl 1,3 propanediol | 16.2 | 9.5 | 20.4 | 27.7 |
| 2 methyl 2,4 pentanediol | 16.4 | 8 | 20.6 | 27.5 |
| 1,2 butanediol | 16 | 8.7 | 19.5 | 26.7 |
| 2,2 dimethyl 1,3 propanediol | 15.9 | 10 | 18.8 | 26.6 |

In some embodiments, the composition comprises at least one polyol solvent having a total Hansen Solubility Parameter (HSP) of from about 23 to 28, including those having an HSP of from 23.5 to about 28, from about 25 to about 28, from about 25 to 27.5, from about 26 to about 28, from about 26 to 27.8, and from 26.6 to 27.8, from about 26 to 27.5, and from 26.6 to 27.5.

In some embodiments, the solvent is selected from 2 methyl 2,4 pentanediol, 1,2 butanediol, 2,2 dimethyl 1,3 propanediol, 1,3-butanediol and mixtures of two or more thereof. In certain embodiments, the solvent is selected from 2 methyl 2,4 pentanediol, 1,2 butanediol, 2,2 dimethyl 1,3 propanediol, and mixtures of two or more thereof.

According to certain embodiments the total amount of polyol solvent(s) in the composition having a total Hansen Solubility Parameter (HSP) of from about 23 to 28 is from about 5% to about 30% by weight of the composition, including from about 5% to about 25%, from about 5% to about 20%, from about 10% to about 30%, from about 10% to about 25%, from about 15% to about 25%, and from about 15% to about 30% by weight of the composition.

Non-Anionic Bioactive Agents

In compositions of the present invention the enhanced antimicrobial efficacy of the non-alcohol mouth rinse is attributed to the presence of a non-anionic bioactive agent phase. Typical examples of such agents, useful when considering anticaries, antiplaque, antigingivitis or gum disease treatment (or symptom reduction) effectiveness, safety and formulation, are:

I. Antimicrobial non-anionic bioactive agents such as:
Halogenated Diphenyl Ethers
2',4,4'-trichloro-2-hydroxy-diphenyl ether (Triclosan)
2,2'-dihydroxy-5,5'-dibromo-diphenyl ether.
Halogenated Salicylanilides
4'5-dibromosalicylanilide
3,4',5-trichlorosalcylanilide
3,4',5-tribromosalicylanilide
2,3,3',5-tetrachlorosalicylanilide
3,3',5-tetrachlorosalicylanilide
3,5-dibromo-3'-trifluoromethyl salicylanilide
5-n-octanoyl-3'-trifluoromethyl salicylanilide
3,5-dibromo-4'-trifluoromethyl salicylanilide
3,5-dibromo-3'-trifluoro methyl salicylanilide (Flurophene).
Benzoic Esters
Methyl-p-Hydroxybenzoic Ester
Ethyl-p-Hydroxybenzoic Ester
Propyl-p-Hydroxybenzoic Ester
Butyl-p-Hydroxybenzoic Ester.
Halogenated Carbanilides
3,4,4'-trichlorocarbanilide
3-trifluoromethyl-4,4'-dichlorocarbanilide
3,3',4-trichlorocarbanilide.
Phenolic Compounds (including phenol and its homologs, mono- and poly-alkyl and aromatic halo (e.g. F, Cl, Br, I)-phenols, resorcinol and catechol and their derivatives and bisphenolic compounds). Such phenolic compounds includes inter alia:
Phenol And Its Homologs
Phenol
2 Methyl-Phenol
3 Methyl-Phenol
4 Methyl-Phenol
4 Ethyl-Phenol
2,4-Dimethyl-Phenol
2,5-Dimethyl-Phenol
3,4-Dimethyl-Phenol
2,6-Dimethyl-Phenol
4-n-Propyl-Phenol
4-n-Butyl-Phenol
4-n-Amyl-Phenol
4-tert-Amyl-Phenol
4-n-Hexyl-Phenol
4-n-Heptyl-Phenol
2-Methoxy-4-(2-Propenyl)-Phenol (Eugenol)
Mono- And Poly-Alkyl And Aralkyl Halophenols
Methyl-p-Chlorophenol
Ethyl-p-Chlorophenol n-Propyl-p-Chlorophenol
n-Butyl-p-Chlorophenol
n-Amyl-p-Chlorophenol
sec-Amyl-p-Chlorophenol
n-Hexyl-p-Chlorophenol
Cyclohexyl-p-Chlorophenol
n-Heptyl-p-Chlorophenol
n-Octyl-p-Chlorophenol
O-Chlorophenol
Methyl-o-Chlorophenol
Ethyl-o-Chlorophenol
n-Propyl-o-Chlorophenol
n-Butyl-o-Chlorophenol
n-Amyl-o-Chlorophenol
tert-Amyl-o-Chlorophenol
n-Hexyl-o-Chlorophenol
n-Heptyl-o-Chlorophenol
p-Chlorophenol
o-Benzyl-p-Chlorophenol
o-Benzyl-m-methyl-p-Chlorophenol
o-Benzyl-m,m-dimethyl-p-Chlorophenol
o-Phenylethyl-p-Chlorophenol
o-Phenylethyl-m-methyl-p-Chlorophenol
3-Methyl-p-Chlorophenol
3,5-Dimethyl-p-Chlorophenol
6-Ethyl-3-methyl-p-Chlorophenol
6-n-Propyl-3-methyl-p-Chlorophenol
6-iso-Propyl-3-methyl-p-Chlorophenol
2-Ethyl-3,5-dimethyl-p-Chlorophenol
6-sec Butyl-3-methyl-p-Chlorophenol
2-iso-Propyl-3,5-dimethyl-p-Chlorophenol
6-Diethylmethyl-3-methyl-p-Chlorophenol
6-iso-Propyl-2-ethyl-3-methyl-p-Chlorophenol
2-sec Amyl-3,5-dimethyl-p-Chlorophenol
2-Diethylmethyl-3,5-dimethyl-p-Chlorophenol
6-sec Octyl-3-methyl-p-Chlorophenol
p-Bromophenol
Methyl-p-Bromophenol
Ethyl-p-Bromophenol
n-Propyl-p-Bromophenol
n-Butyl-p-Bromophenol
n-Amyl-p-Bromophenol
sec-Amyl-p-Bromophenol
n-Hexyl-p-Bromophenol
cyclohexyl-p-Bromophenol
o-Bromophenol
tert-Amyl-o-Bromophenol
n-Hexyl-o-Bromophenol
n-Propyl-m,m-Dimethyl-o-Bromophenol
2-Phenyl Phenol
4-chloro-2-methyl phenol
4-chloro-3-methyl phenol
4-chloro-3,5-dimethyl phenol
2,4-dichloro-3,5-dimethylphenol
3,4,5,6-terabromo-2-methylphenol
5-methyl-2-pentylphenol
4-isopropyl-3-methylphenol
5-chloro-2-hydroxydiphenylemthane.
Resorcinol And Its Derivatives
Resorcinol
Methyl-Resorcinol
Ethyl-Resorcinol
n-Propyl-Resorcinol
n-Butyl-Resorcinol
n-Amyl-Resorcinol
n-Hexyl-Resorcinol
n-Heptyl-Resorcinol n-Octyl-Resorcinol
n-Nonyl-Resorcinol
Phenyl-Resorcinol
Benzyl-Resorcinol
Phenylethyl-Resorcinol
Phenylpropyl-Resorcinol
p-Chlorobenzyl-Resorcinol
5-Chloro-2,4-Dihydroxydiphenyl Methane
4'-Chloro-2,4-Dihydroxydiphenyl Methane
5-Bromo-2,4-Dihydroxydiphenyl Methane
4'-Bromo-2,4-Dihydroxydiphenyl Methane.
Bisphenolic Compounds
Bisphenol A
2,2'-methylene bis(4-chlorophenol)
2,2'-methylene bis(3,4,6-trichlorophenol) (hexachlorophene)
2,2'-methylene bis(4-chloro-6-bromophenol)
bis(2-hydroxy-3,5-dichlorophenyl) sulfide
bis(2-hydroxy-5-chlorobenzyl) sulfide.

Other antimicrobial non-anionic bioactive agents include, but are not limited to: hexetidine; fatty acid compounds such as caproic acid, caprilic acid, capric acid, lauric acid, myristic acid, myristoleic acid, palmitic acid, palmitoleic acid, stearic acid, oleic acid, elaidic acid, linoleic acid, linolenic acid, linolelaidic acid, arachidonic acid vitamin E, vitamin E acetate, apigenin and mixtures thereof; long chain fatty alcohols such as described in US Patent publication US 20110123462 to Mordas et al., herein incorporated by reference in its entirety, (examples of which include, but are not limited to 1-decen-3-ol; cis-4-decen-1-ol, trans-2-decen-1-ol, cis-2-nonen-1-ol, cis-4-decenal, trans-2-decenal, cis-7-decenal, cis-5-octen-1-ol, trans-2-octen-1-ol, 1-octen-3-ol, cis-3-nonen-1-ol, trans-2-nonen-1-ol, cis-6-nonen-1-ol, 9-decen-1-ol, trans-2-undecen-1-ol, trans-2-dodecen-1-ol, trans-2-octenal, trans-2-nonenal, 6-nonenal, cis-2-decenal, trans-2-undecenal, trans-2-dodecenal, cis-3-octen-1-ol, 3-octen-2-ol, 10-undecen-1-ol, trans-2-tridecen-1-ol, stereoisomers thereof and mixtures thereof); N'-alkyl-L-arginine alkyl ester (e.g., Lauroyl Arginine Ethyl Ester) and salts such as described in U.S. Pat. No. 5,874,068 to Engelman et al., herein incorporated by reference in its entirety; and surfactants, including cationic surfactants such as cetylpyridinium chloride, chlorhexedine and mixtures thereof. Oils such as peppermint oil and sage oil are also useful herein.

Also useful as antimicrobial non-anionic bioactive agents are one or more bioactive essential oils or mixtures thereof. Nonlimiting examples of such essential oils include: Thymol, [$(CH_3)_2CHC_6H_3(CH_3)OH$, also known as isopropyl-m-cresol], is only slightly soluble in water but is soluble in alcohol, and its presence is one of the reasons alcohol was necessary in the well-established, high alcohol commercial mouth rinses.

Methyl salicylate, [$C_6H_4OHCOOCH_3$, also known as wintergreen oil], additionally provides flavoring to the together with its antimicrobial function.

Eucalyptol ($C_{10}H_{18}O$, also known as cineol) is a terpene ether and provides a cooling, spicy taste. Eucalyptol may be used in place of thymol in certain formulations in the same amount if desired.

Menthol ($CH_3C_6H_9(C_3H_7)OH$), also known as hexahydrothymol) is also only slightly soluble in alcohol, and is fairly volatile. Menthol, in addition to any antiseptic properties, provides a cooling, tingling sensation.

II. Anti-inflammatory non-anionic bioactive agents such as:

NFkB-inhibitor such as substituted resorcinols (such as 4-hexyl resorcinol and 4-octylresorcinol), (E)-3-(4-methylphenylsulfonyl)-2-propenenitrile (such as "Bay 11-7082,"

commercially available from Sigma-Aldrich of St. Louis, Mo.), tetrahydrocurcuminoids (such as Tetrahydrocurcuminoid CG, available from Sabinsa Corporation of Piscataway, N.J.), extracts of *Paulownia tomentosa* wood, and combinations thereof phellodendron *amurense* cortex extract (PCE), feverfew (*Tanacetum parthenium*), ginger (*Zingiber officinale*), ginko (*Ginko Biloba*), cotinus (*Cotinus coggygria*), goji berry (*Lycium barbarum*), milk thistle extract (*Silybum marianum*), honeysuckle (*Lonicera japonica*), basalm of Peru (*Myroxylon pereirae*), sage (*Salvia officinalis*), cranberry extract (*Vaccinium oxycoccos*), amaranth oil (*Amaranthus cruentus*), pomegranate (*Punica granatum*), yerbe mate (*Ilex paraguariensis* Leaf Extract), white lily flower extract (*Lilium Candidum*), olive leaf extract (*Olea europaea*), phloretin (apple extract), lifenol (hops: *Humulus lupulus*) extract, licochalcone (licorice: *Glycyrrhiza* inflate extract ingredient), symrelief (bisabolol and ginger extract), Magnolol (extract from bark of the *Houpu magnolia* [*Magnolia officinalis*], Honokiol (extract from cones, bark, and leaves of *Magnolia grandifloris*] and mixtures thereof; non-steroidal anti-inflammatory agents such as salicylic acid derivatives (e.g. aspirin) paraminophenol derivative (e.g. acetaminophen) indole and indene acetic acids (indomethacin, sulindac and etodalac) heteroaryl acetic acids (tolmetin diclofenac and ketorolac) aryl propionic acid derivatives (ibuprofen, naproxen, ketoprofen, fenopren, oxaprozine), anthranilic acids (mefenamic acid, meclofenamic acid) enolic acids (piroxicam, tenoxicam, phenylbutazone and oxyphenthatrazone) and mixtures thereof.

Other useful non-anionic bioactive agents can be found in US Patent Publication 2007/0190080 to Doron Friedman and US Patent Publication 20120003162 to Mordas et al., each of which is herein incorporated by reference in its entirety.

Optionally, mixtures of any of the above mentioned compounds can be used as the non-anionic bioactive agent.

The non-anionic bioactive agent is present in the oral composition in an amount effective to achieve biologic activity such as anti-inflammation, analgesic, anticaries, antiplaque, antigingivitis or reduction in the symptoms of gum disease. The effective amount of the non-anionic bioactive agent for i) treating or reducing inflammation or other symptoms of gum disease or ii) providing analgesia, anticaries, antiplaque, antigingivitis ranges from about 0.01%, optionally from about 0.01% to about 5%, optionally from about 0.03% to about 1%, or optionally from about 0.03% to about 0.5%, by weight of the total composition. In certain embodiments, the non-anionic bioactive agent is water-insoluble, or substantially water-insoluble, meaning that its solubility is less than about 1% by weight in water at 25° C. or, optionally, less than about 0.1%. In other embodiments, the non-anionic bioactive agent is defined in terms of the degree of hydrophobicity of the bioactive agent as measured by the partition coefficient (log P) for the non-anionic bioactive agent. In certain embodiments, the bioactive agent has a log P of greater than 2 (or about 2), optionally greater than 3 (or about 3), or optionally greater than 3.5 (or about 3.5), but, optionally, less than 9 (or about 9) or, optionally, less than 7 (or about 7).

Select non-anionic bioactive agents and their calculated log P value using HSPiP software (v3.1.20) are provided in Table 2.

TABLE 2

Calculated log P value using HSPiP software (v3.1.20).

| Non-Anionic Bioactive Agent | Calculated Log P |
|---|---|
| Menthol | 2.89 |
| Thymol | 3.23 |
| Methyl Salicylate | 2.29 |
| Eucalyptol | 3.23 |
| Triclosan | 4.51 |
| Cetyl Pyridiunium Chloride | 8.42 |
| Hexetidine | 5.98 |
| Lauroyl Arginine Ethyl Ester | 5.31 |
| cis-2-nonen-1-ol | 3.01 |
| 1-decen-3-ol | 3.63 |
| trans-2-dodecenal | 4.75 |
| cis-4-decenal | 3.51 |
| trans-2-decenal | 3.70 |

In certain embodiments, the non-anionic bioactive agent comprises at least one antimicrobial or bioactive essential oils including, but not limited to thymol, eucalyptol, menthol and methyl salicylate, and combinations thereof.

In certain embodiments, the essential oils are used in amounts effective to provide antimicrobial activity in the oral cavity. In specific embodiments, the total amount of essential oils present in the disclosed compositions can be from 0.001% (or about 0.001%) to 0.35% (or about 0.35%) w/v, or optionally from 0.16% (or about 0.16%) to 0.28% (or about 0.28%) w/v of the composition.

In some embodiments, the compositions of the present invention contain thymol and additionally eucalyptol, menthol, or methyl salicylate, or mixtures thereof. Optionally, the composition contains all four of these essential oils.

In certain embodiments, thymol is employed in amounts of from 0.001% (or about 0.001%) to 0.25% (or about 0.25%) w/v, or optionally from 0.04% (or about 0.04%) to 0.07% (or about 0.07%) w/v of the composition. In certain embodiments, eucalyptol may be employed in amounts of from 0.001% (or about 0.001%) to 0.11% (or about 0.11%) w/v, or optionally from 0.085% (or about 0.085%) to 0.10% (or about 0.10%) w/v of the composition. In certain embodiments, menthol is employed in amounts of from 0.001% (or about 0.001%) to 0.25% (or about 0.25%) w/v, or optionally from 0.035% (or about 0.035%) to 0.05% (or about 0.05%) w/v of the composition. In certain embodiments, methyl salicylate is employed in amounts of from 0.001% (or about 0.001%) to 0.08% (or about 0.08%) w/v, or optionally from 0.04% (or about 0.04%) to 0.07% (or about 0.07%) w/v of the composition.

In known antimicrobial mouth rinses, the carrier for the essential oils (the active ingredients) is typically a water-alcohol mixture, generally water-ethanol. In the past, some antiseptic oral mouth rinse compositions, required ethanol levels of up to about 27% v/v. These high levels were necessary to assist the actives in providing the necessary antimicrobial functionality as well as providing a clear, aesthetically attractive liquid medium. Merely reducing the alcohol levels, without the addition of other formulation components, results in a cloudy, less efficacious product.

Without being bound to any theory, it is believed that in these high alcohol level oral compositions, the alcohol solubilizes the antimicrobial essential oils and in so doing acts by an active enhancement mechanism. The antimicrobial essential oils are more readily dispersed throughout the solution and remain free or unbound to attack pathogenic microbes throughout the oral cavity. Reducing the alcohol levels was believed to adversely affect this enhancement mechanism. In accordance with the present invention, however, it was surprisingly and unexpectedly found that the level of alcohol can be reduced or eliminated without sacrificing antimicrobial efficacy or clarity if the mouth rinse composition contains the non-alcohol solvents as taught herein.

In certain embodiments, the total amount of oil phase present in the disclosed compositions of the present invention should not exceed 1.35% w/v (or about 1.35% w/v) of the mouth rinse composition. Optionally, the total oil phase, can be present in an amount of from 0.04% (or about 0.04%) to 1.35% (or about 1.35%) w/v, or optionally from 0.10% (or about 0.10%) to 0.4% (or about 0.4%) w/v of the mouth rinse composition.

Aqueous Phase

An aqueous phase comprising water is added to the oil phase of the present compositions to form oil-in-water or water-in-oil dispersions, micro emulsions or emulsions.

In certain embodiments, the aqueous phase comprises from about 60% to about 99%, including from about 75% to about 99%, from about 85% to 99%, or optionally from about 75% to about 93%, by weight of the composition. In certain embodiments the total amount of water in the composition is from about 60 to about 90%, including from about 75 to about 90% water, and from about 80% to 90% water.

Alternatively, the mouth rinse compositions of the present invention may be formulated in a dry powder, chewing gum, semi-solid, solid or liquid concentrate form. In such embodiments, for example, water is added to q.s. as necessary in the case of liquid concentrates or powdered formulations, or water may be removed using standard evaporation procedures known in the art to produce a composition in dry powder form. Evaporated, or freeze dried forms are advantageous for storage and shipping.

Surfactants

In certain embodiments, the present compositions are free of or essentially free of alkyl sulfate surfactants. Alkyl sulfate surfactants include, but are not limited to sulfated $C_8$ to $C_{18}$, optionally sulfated $C_{10}$ to $C_{16}$ even numbered carbon chain length alcohols neutralized with a suitable basic salt such as sodium carbonate or sodium hydroxide and mixtures thereof such that the alkyl sulfate surfactant has an even numbered $C_8$ to $C_{18}$, optionally $C_{10}$ to $C_{16}$, chain length. In certain embodiments, the alkyl sulfate is selected from the group consisting of sodium lauryl sulfate, hexadecyl sulfate and mixtures thereof. "Essentially free" as used with respect to alkyl sulfate surfactants is defined as formulations having less than 2% (or about 2%), optionally, 1% (or about 1%), or optionally 0.1, or optionally, 0.01% (or about 0.01%), by weight (w/v) of the total composition of alkyl sulfate surfactants. Optionally, the compositions of the present invention are free of alkyl sulfate surfactants.

In certain embodiments of the present composition, surfactants may be incorporated to aid in the solubilization of the hydrophobic actives. The amount of the surfactant added to the composition can be from 0.05% (or about 0.05%) to 2.0% (or about 2.0%) w/v, or optionally from 0.1% (or about 0.1%) to 0.5% (or about 0.5%) w/v of the composition.

Suitable examples include anionic surfactants, nonionic surfactants, amphoteric surfactants and mixtures thereof. However, in certain embodiments, the total surfactant concentration of the mouth rinses of the present invention is about 3% w/w % or less, optionally, the total surfactant concentration is about 2% w/w or less, or about 1.5% or less, optionally, the total surfactant concentration is about 1% w/w or less, optionally, the total surfactant concentration is about 0.5% w/w or less by weight of the composition, optionally, the total surfactant concentration is about 0.25% w/w or less, or optionally, the total surfactant concentration is about 0.2% w/w or less.

Anionic surfactants useful herein include, but are not limited to, sarcosine type surfactants or sarcosinates such as sodium lauroyl sarcosinate; taurates such as sodium methyl cocoyl taurate; sodium lauryl sulfoacetate; sodium lauroyl isethionate; sodium laureth carboxylate; sodium laureth sulphate; sodium dodecyl benzenesulfonate and mixtures thereof. Many suitable anionic surfactants are disclosed in U.S. Pat. No. 3,959,458, to Agricola, et al., herein incorporated by reference in its entirety. In some embodiments, the anionic surfactant is an alkyl ether sulfate, such as sodium laureth sulphate and the like.

Nonionic surfactants which can be used in the compositions of the present invention include, but are not limited to, compounds produced by the condensation of alkylene oxide groups (hydrophilic in nature) with an organic hydrophobic compound which may be aliphatic or alkyl-aromatic in nature. Examples of suitable nonionic surfactants include, but are not limited to, alkyl polyglucosides; ethoxylated hydrogenated castor oils available commercially for example under the trade name CRODURET (Croda Inc., Edison, N.J.), and/or; fatty alcohol ethoxylates; polyethylene oxide condensates of alkyl phenols; products derived from the condensation of ethylene oxide with the reaction product of propylene oxide and ethylene diamine; ethylene oxide condensates of aliphatic alcohols; long chain tertiary amine oxides; long chain tertiary phosphine oxides; long chain dialkyl sulfoxides; poloxamers, such as Poloxamer 407, Poloxamer 188, Poloxamer 108, and mixtures thereof. In some embodiments, the nonionic surfactant is sodium Poloxamer 407. In some embodiments, the nonionic surfactant is sodium Poloxamer 188.

The amphoteric surfactants useful in the present invention include, but are not limited to, derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Examples of suitable amphoteric surfactants include, but are not limited to alkylimino-diproprionates, alkylamphoglycinates (mono or di), alkylamphoproprionates (mono or di), alkylamphoacetates (mono or di), N-alkyl β-aminoproprionic acids, alkylpolyamino carboxylates, phosphorylated imidazolines, alkyl betaines, alkylamido betaines, alkylamidopropyl betaines, cocoamdiopropyl betaines, alkyl sultaines, alkylamido sultaines, and mixtures thereof. In certain embodiments, the amphoteric surfactant is selected from the group consisting of alkylamidopropyl betaines, amphoacetates such as sodium lauroamphoacetate and mixtures thereof. Mixtures of any of the above mentioned surfactants can also be employed. A more detailed discussion of anionic, nonionic and amphoteric surfactants can be found in U.S. Pat. No. 7,087,650 to Lennon; U.S. Pat. No. 7,084,104 to Martin et al.; U.S. Pat. No. 5,190,747 to Sekiguchi et al.; and U.S. Pat. No. 4,051,234, Gieske, et al., each of which patents are herein incorporated by reference in their entirety.

In certain embodiments, the additional surfactant to be added the mouth rinses of the present invention with the alkyl sulfate surfactant is selected from the group consisting of taurates. Optionally, the additional surfactant is selected from the group consisting of sodium methyl lauryl taurate, sodium methyl oleoyl taurate, sodium methyl cocoyl taurate and mixtures thereof. In certain embodiments, the additional surfactant is sodium methyl cocoyl taurate.

Sugar Alcohol Solvents

According to certain embodiments, the compositions of the present invention comprise one or more sugar alcohol solvents. The sugar alcohol solvent(s) may be selected from those multi-hydroxy-functional compounds that are conventionally used in oral and ingestible products. In certain embodiments, the sugar alcohol (s) should be non-metabolized and non-fermentable sugar alcohol (s). In specific embodiments, the sugar alcohols include, but are not limited to sorbitol, xylitol, mannitol, maltitol, inositol, allitol, altritol, dulcitol, galactitol, glucitol, hexitol, iditol, pentitol, ribitol, erythritol and mixtures thereof. In certain embodiments, the sugar alcohol is selected from the group consisting of sorbitol and xylitol or mixtures thereof. In certain embodiments, the sugar alcohol comprises sorbitol. In certain embodiments, the total amount of sugar alcohol (s) which are added comprise about 30% w/v or less of the composition. In certain embodiments, the total amount of sugar alcohol is about 20% w/v or less of the composition. The sugar alcohol can be in an amount of from about 1.0% to about 30.0% w/v, including from about 10.0% to about 30.0%, about 10.0% to about 20.0%, about 7% to about 30% w/v, about 7%, about 10% w/v, about 14% w/v, about 20% w/v, about 21% w/v, or about 30% w/v of the composition.

Micelle Size

The mouth rinse compositions of the present invention comprise colloidal aggregates of amphipathic molecules called micelles. In certain embodiments, the micelles of the present invention have an aggregate size of less than 200 nm (or about 200 nm), optionally 100 nm (or about 100 nm), optionally 50 nm (or about 50 nm), or optionally 10 nm (or about 10).

Optional Ingredients

Insoluble Particulates

In certain embodiments, the oral care compositions of the present invention optionally comprise a safe and effective amount of a water insoluble particulate. The water insoluble particulate can be an abrasive particle (such as a dentally acceptable abrasive) or non-abrasive particulate.

In certain embodiments, dentally acceptable abrasives include, but are not limited to, water insoluble calcium salts such as calcium carbonate, and various calcium phosphates, alumina, silica, synthetic resins and mixtures thereof. Suitable dentally acceptable abrasives may generally be defined as those having a radioactive dentine abrasion value (RDA) of from about 30 to about 250 at the concentrations used in the compositions of the present invention. In certain embodiments, abrasives are non-crystalline, hydrated, silica abrasives, particularly in the form of precipitated silica or milled silica gels available commercially, for example, under the trade names ZEODENT (J. M. Huber Corporation, Edison, N.J.), and SYLODENT (W.R. Grace & Co., New York, N.Y.), respectively. In certain embodiments, the compositions according to the present invention comprise from about 1% to about 20%, or, optionally, from about 5% to about 10% by weight of the abrasive.

Alternatively, the insoluble particulate is a non-abrasive particulate which is visible to the unaided eye and stable in the compositions of the present invention.

The non-abrasive particulate can be of any size, shape, or color, according to the desired characteristic of the product. The non-abrasive particulates will typically have the shape of a small round or substantially round ball or sphere, however, platelet or rod-shaped configurations are also contemplated herein. Generally, a non-abrasive particulate has an average diameter of from about 50 µm to about 5000 µm, optionally from about 100 µm to about 3000 µm, or optionally from about 300 µm to about 1000 µm. By the terms "stable" and/or "stability", it is meant that the abrasive or non-abrasive particulates are not disintegrated, agglomerated, or separated under normal shelf conditions. In certain embodiments, the terms "stable" and/or "stability" further mean that the compositions of present invention contain no visible or minimally visible (to the unaided eye) signs of sedimentation of the insoluble particulates after 8 weeks, optionally 26 weeks, optionally 52 weeks, at room temperature.

The non-abrasive particulates herein are typically incorporated in the present compositions at levels of from about 0.01% to about 25%, optionally, from about 0.01% to about 5%, or optionally, from about 0.05% to about 3%, by weight of the composition.

The non-abrasive particulate herein will typically comprise a structural material and/or, optionally, an encompassed material.

The structural material provides a certain strength to the non-abrasive particulates so that they retain their distinctively detectable structure in the compositions of the present invention under normal shelf conditions. In one embodiment, the structural material further can be broken and disintegrated with very little shear on the teeth, tongue or oral mucosa upon use.

The non-abrasive particulates can be solid or liquid, filled or un-filled, as long as they are stable in the compositions of the present invention. The structural material used for making the non-abrasive particulates varies depending on the compatibility with other components, as well as material, if any, to be encompassed in the non-abrasive particulates. Exemplary materials for making the non-abrasive particulates herein include: polysaccharide and saccharide derivatives such as crystalline cellulose, cellulose acetate, cellulose acetate butyrate, cellulose acetate phthalate, cellulose nitrate, ethylcellulose, hydroxypropylcellulose, hydroxypropylmethylcellulose, hydroxypropylmethylcellulose phthalate, methyl cellulose, sodium carboxymethylcellulose, gum acacia (gum arabic), agar, agarose, maltodextrin, sodium alginate, calcium alginate, dextran, starch, galactose, glucosamine, cyclodextrin, chitin, amylose, amylopectin, glycogen, laminaran, lichenan, curdlan, inulin, levan, pectin, mannan, xylan, alginic acid, arabic acid, glucommannan, agarose, agaropectin, prophyran, carrageenen, fucoidan, glycosaminoglycan, hyaluronic acid, chondroitin, peptidoglycan, lipopolysaccharide, guar gum, starch, and starch derivatives; oligosaccharides such as sucrose, lactose, maltose, uronic acid, muramic acid, cellobiose, isomaltose, planteose, melezitose, gentianose, maltotriose, stachyose, glucoside and polyglucoside; monosaccharides such as glucose, fructose, and mannose; synthetic polymers such as acrylic polymers and copolymers including polyacrylamide, poly (alkyl cyanoacrylate), and poly(ethylene-vinyl acetate), and carboxyvinyl polymer, polyamide, poly(methyl vinyl ether-maleic anhydride), poly(adipyl-L-lysine), polycarbonate, polyterephthalamide, polyvinyl acetate phthalate, poly(terephthaloyl-L-lysine), polyarylsulfone, poly(methylmethacrylate), poly(ε-caprolactone), polyvinylpyrrolidone, polydimethylsiloxane, polyoxyethylene, polyester, polyglycolic acid, polylactic acid, polyglutamic acid, polylysine, polystyrene, poly(styrene-acrylonitrile), polyimide, and poly(vinyl alcohol); and other material such as fat, fatty acid, fatty alcohol, milk solids, molasses, gelatin, gluten, albumin, shellac, caseinate, bees wax, carnauba wax, spermaceti wax, hydrogenated tallow, glycerol monopalmitate, glycerol dipalmitate, hydrogenated castor oil, glycerol monostearate, glycerol distearate, glycerol tristearate, 12-hydroxystearyl alcohol, protein, and protein derivatives; and mixtures thereof. Components herein may be described in other sections as useful components for the present composition. In certain embodiments, the components as described in this section form the structure of the non-abrasive particulates so as to not be substantially dissolved or dispersed from the particulates and into the compositions of the present invention under normal shelf conditions.

In other embodiments, the structural material herein comprises components selected from the group consisting of polysaccharides and their derivatives, saccharides and their derivatives, oligosaccharides, monosaccharides, and mixtures thereof, or optionally, comprises components are having various degrees of water solubility. In some embodiments, the structural material comprises lactose, cellulose, and hydroxypropyl methylcellulose.

Suitable non-abrasive particulates also include organogel particles as described in detail in U.S. Pat. No. 6,797,683, herein corporate by reference in its entirety. Non-abrasive particulates that are organogel particles typically comprise a structural material selected from waxes (e.g., beeswax, paraffin, water-insoluble wax, carbon-based wax, silicone wax, microcrystalline wax, etc.), triglycerides, acid triglycerides, polymers, fluoroalkyl (meth)acrylate polymers and copolymers, acrylate polymers, ethylene/acrylate copolymers, polyethylene, polypropylene polymers and copolymers, fatty acids, fatty alcohols, fatty acid esters, fatty acid ethers, fatty acid amides, alkylene polyhydric alcohols, fatty acid amide of an alkanolamine, glyceryl monostearate, (aryl-substituted) sugars, dibenzyl sorbitol (or mannitoal, rabbitol, etc.), condensates and precondensates of lower monohydric alcohols, trihydroic alcohols, lower polyglycols, propylene/ethylene polycondensates, and the like. Optionally, structural material for non-abrasive particulates that are organogel particles include beeswax, carnauba wax, low molecular weight ethylene homopolymers (e.g. Polywax 500, Polywax 1000, or Polywax 2000 polyethylene materials available from Baker Petrolite Corp.), or paraffin wax.

The non-abrasive particulates herein may encompass, contain, or be filled with an encompassed material. Such encompassed material can be water soluble or water insoluble. Suitable encompassed materials include benefit agents as described herein such as: oral care actives, vitamins, pigments, dyes, antimicrobial agents, chelating agents, optical brighteners, flavors, perfumes, humectants, minerals, and mixtures thereof. The encompassed materials herein are substantially retained within the non-abrasive particulates, and are substantially not dissolved from the particulates and into the compositions of the present composition under normal shelf conditions.

Particularly useful commercially available non-abrasive particulates herein are those with tradenames Unisphere and Unicerin available from Induchem AG (Switzerland), and Confetti Dermal Essentials available from United-Guardian Inc. (NY, USA). Unisphere and Unicerin particles are made of microcrystalline cellulose, hydroxypropyl cellulose, lactose, vitamins, pigments, and proteins. Upon use, the Unisphere and Unicerin particles can be disintegrated with very little shear and with practically no resistance, and readily disperse in the compositions of the present invention.

Suitable non-abrasive particulates for incorporation in the present compositions are described in detail in U.S. Pat. No. 6,797,683 (organogel particles); U.S. Pat. No. 6,045,813 (rupturable beads); U.S. Pat. Publ. 2004/0047822 A1 (visible capsules); and U.S. Pat. No. 6,106,815 (capsulated or particulated oily substances), each of which patent documents are herein incorporated by reference in their entirety.

In certain embodiments, the abrasive and/or nonabrasive particles have a density different or, optionally, substantially different from the carrier in which these particles are formulated.

Flavors or Flavorants

In certain embodiments, flavors or flavorants may also be added to further modify or magnify the taste of the mouth rinse, or reduce or mask the sharp "bite" or "burn" of ingredients such as thymol. Suitable flavors include, but are not limited to, oil of anise, anethole, benzyl alcohol, spearmint oil, citrus oils, vanillin and the like may be incorporated. In these embodiments, the amount of flavor oil added to the composition can be from 0.001% (or about 0.001%) to 1.0% (or about 1.0%) w/v, or optionally from 0.1% (or about 0.10%) to 0.30% (or about 0.30%) w/v of the composition.

The particular flavors or flavorants, and other taste-improving ingredients, employed will vary depending upon the particular taste and feel desired. Those skilled in the art can select and customize these types of ingredients to provide the desired results.

Buffers

In certain embodiments, additional conventional components may be added as in mouthwashes and mouth rinses of the prior art. Whereas some alcohol containing mouth rinses have a pH of about 7.0, reduction of the alcohol level may require the addition of acidic preservatives, such as sorbic acid or benzoic acid, which reduce pH levels. Buffer systems are then necessary to control the pH of the composition at optimal levels. This is generally accomplished through the addition of a weak acid and its salt or a weak base and its salt. In some embodiments, useful systems have been found to be sodium benzoate and benzoic acid in amounts of from 0.01% (or about 0.01% w/v) to 1.0% w/v (or about 1.0% w/v) of the composition, and sodium citrate and citric acid in amounts of from 0.001% (or about 0.001% w/v) to 1.0% w/v (or about 1.0% w/v) of the composition, phosphoric acid and sodium/potassium phosphate of amounts from 0.01% (or about 0.01%) to 1.0% (or about 1.0%) by weight of the composition. In certain embodiments, the buffers are incorporated in amounts that maintain the pH at levels of from 3.0 (or about 3.0) to 8.0 (or about 8.0), optionally from 3.5 (or about 3.5) to 6.5 (or about 6.5), optionally from 3.5 (or about 3.5) to 5.0 (or about 5.0). Without being limited by any theory, it is believed that these pH levels provide the essential oils with an environment that also maximizes their antimicrobial activity and promotes stability.

Fluoride Releasing Compounds

In certain embodiments, fluoride providing compounds may be present in the mouth rinse compositions of this invention. These compounds may be slightly water soluble or may be fully water soluble and are characterized by their ability to release fluoride ions or fluoride containing ions in water. Typical fluoride providing compounds are inorganic fluoride salts such as soluble alkali metal, alkaline earth metal, and heavy metal salts, for example, sodium fluoride, potassium fluoride, ammonium fluoride, cupric fluoride, zinc fluoride, stannic fluoride, stannous fluoride, barium fluoride, sodium hexafluorosilicate, ammonium hexafluorosilicate, sodium fluorozirconate, sodium monofluorophosphate, aluminum mono- and difluorophosphate and fluorinated sodium calcium pyrophosphate. Amine fluorides, such as N'-octadecyltrimethylendiamine-N,N,N'-tris(2-ethanol)-dihydrofluoride and 9-octadecenylamine-hydrofluoride), may also be used.

In certain embodiments, the fluoride providing compound is generally present in an amount sufficient to release up to 0.15% (or about 0.15%), optionally 0.001% (or about 0.001%) to 0.1% (or about 0.1%), optionally from 0.001% (or about 0.001%) to 0.05% (or about 0.05%) fluoride by weight of the composition.

Zinc Salts

In certain embodiments, zinc salts such as zinc chloride, zinc acetate or zinc citrate may be added as an astringent for an "antiseptic cleaning" feeling, as a breath protection enhancer or as anticalculus agent in an amount of from 0.0025% w/v (or about 0.0025% w/v) to 0.1% w/v (or about 0.1% w/v) of the composition.

Sensitivity Reducing Agents

In certain embodiments, sensitivity reducing agents, namely potassium salts of nitrate and oxalate in an amount from 0.1% (or about 0.1%) to 5.0% (or about 5.0%) w/v of the composition may be incorporated into the present invention. Other potassium releasing compounds are feasible (e.g. KCl). High concentrations of calcium phosphates may also provide some added sensitivity relief. These agents are believed to work by either forming an occlusive surface mineral deposit on the tooth surface or through providing potassium to the nerves within the teeth to depolarize the nerves. A more detailed discussion of suitable sensitivity reducing can be found in US 20060013778 to Hodosh and U.S. Pat. No. 6,416,745 to Markowitz et al., both of which are herein incorporated by reference in their entirety.

Anticalculus Agents

In certain embodiments, compounds with anti-calculus benefits (e.g. polyphosphates, phosphonates, various carboxylates, polyaspartic acid, inositol phosphate etc.) may be incorporated into the present invention. Also useful as an anticalculus agent are the anionic polymeric polycarboxylates. Such materials are well known in the art, being employed in the form of their free acids or partially or preferably fully neutralized water soluble alkali metal (e.g. potassium and preferably sodium) or ammonium salts. Preferred are 1:4 to 4:1 by weight copolymers of maleic anhydride or acid with another polymerizable ethylenically unsaturated monomer, preferably methyl vinyl ether (methoxyethylene) having a molecular weight (M.W.) of about 30,000 to about 1,000,000. These copolymers are available for example as Gantrez AN 139 (M.W. 500,000), AN 119 (M.W. 250,000) and preferably S-97 Pharmaceutical Grade (M.W. 70,000), of GAF Chemicals Corporation.

Additional Ingredients

Although the mouth rinse compositions of the present invention may be formulated to be substantially clear and/or colorless to the unaided eye, acceptably approved food dyes are preferably used to provide a pleasing color to the compositions of the invention. These may be selected from, but not limited to, the long list of acceptable food dyes. Suitable dyes for this purpose include FD&C yellow #5, FD&C yellow #10, FD&C blue #1 and FD&C green #3. These are added in conventional amounts, typically in individual amounts of from 0.00001% w/v (or about 0.00001% w/v) to 0.0008% w/v (or about 0.0008% w/v), optionally from 0.00035% w/v (or about 0.00035% w/v) to 0.0005% w/v (or about 0.0005% w/v) of the composition.

Other conventional ingredients may be used in the mouth rinse compositions of this invention, including those known and used in the art. Examples of such ingredients include thickeners, suspending agents and softeners. Thickeners and suspending agents useful in the compositions of the present invention can be found in U.S. Pat. No. 5,328,682 to Pullen et al., herein incorporated by reference in its entirety. In certain embodiments, these are incorporated in amounts of from 0.1% w/v (about 0.1% w/v) to 0.6% w/v (or about 0.6% w/v), optionally 0.5% w/v (or about 0.5% w/v) of the composition.

Methods of Practicing the Present Invention

The invention illustratively disclosed herein may be practiced in the absence of any component, ingredient, or step which is not specifically disclosed herein.

In some embodiments, the present invention relates to methods of treating plaque, gingivitis, gum disease, or oral malodor, comprising the step of applying to the tissues (i.e., soft and hard) of the oral cavity of a mammal in need of such treatment the oral composition of the present invention in an amount effective to reduce or prevent tooth decay and/or reduce or prevent the symptoms associated with plaque, gingivitis or gum disease.

In further embodiments, the present invention relates to methods of treating or reducing symptoms associated with inflamed tissue, comprising the step of applying to the tissues of a mammal in need of such treatment an amount of the composition of the present invention effective to reduce symptoms associated inflammation.

In still further embodiments, the present invention relates to methods for reducing the number of oral microorganisms responsible for plaque, gingivitis, gum disease or oral malodor, comprising the step of applying to the tissues of the oral cavity of a mammal having such microorganisms an amount of the composition of the present invention effective to reduce the number of such oral microorganisms.

In certain embodiments, the compositions of the present invention are applied to teeth and/or soft surfaces of the oral cavity for at least two consecutive applications, optionally, at least (or greater than) 3 (or about 3) or optionally, at least (or greater than) 5 (or about 5) consecutive applications.

When applied to teeth and/or soft surfaces of the oral cavity, in certain embodiments, the composition is allowed to remain in contact with the teeth and/or soft surfaces of the oral cavity for at least (or greater than) 10 (or about 10) seconds, optionally 20 (or about 20) seconds, optionally 30 (or about 30) seconds, optionally 50 (or about 50) seconds, or optionally 60 (or about 60) seconds.

Various embodiments of the invention have been set forth above. Each embodiment is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents.

EXAMPLES

Example 1

The efficacy of biofilm kill with 1% active Sodium Laureth Sulfate surfactant in an in-vitro single species *S. mutans* biofilm model.

The nine tested formulations included:
0.0323% Menthol USP (essential oil)
0.0639% Thymol NF (essential oil)
0.0922% Eucalyptol USP (essential oil)
0.0660% Methyl Salicylate NF (essential oil)
0.0850% Mint Flavor N & A (flavor/essential oil)

20% Sorbitol Solution USP (70%) (sugar alcohol)
0.1170% Saccharin Sodium USP Granular (sweetener)
0.1200% Benzoic Acid USP (pH adjustment)
0.0354% Sodium Benzoate (pH adjustment)
q.s. water
1% active Sodium Laureth Sulfate (non-ionic surfactant), and
20% solvent.

Mouth rinse formulations described above were prepared and tested using an in vitro single-species *S. mutans* biofilm model. A 22-hour *S. mutans* biofilm was grown (N=24) and exposed to the formulation for thirty seconds. After treatment, the biofilm was neutralized and rinsed. The biofilm was harvested via sonication using a Misonix XL-2000 Ultrasonic processor (Qsonica, LLC, Newtown, Conn.). Using a Celsis Rapid Detection RapiScreen kit (Celsis International PLC, Chicago). The bacteria was lysed with Celsis Luminex and then the adenosine triphosphate (ATP) from the bacteria was measured using the bioluminescence marker Celsis LuminATE. ATP concentration was measured by RLUs (relative light units) which is an indication of cell viability. Decreasing log RLUs indicates fewer bacteria alive after treatment. Decreasing log RLUs Sterile water negative controls usually yield a log RLU of between 7.0 and 8.0, while the positive control (a commercially available essential oil mouth rinse) usually yield a log RLU of between 5.5 and 6.5.

Table 3 shows the in-vitro single species *S. mutans* biofilm model kill results with respect to the total Hansen Solubility Parameter (HSP) value for the nine formulations with 20% solvent loading and 1% active Sodium Laureth Sulfate (SLES) surfactant. Final formulations were adjusted to pH 4.2 with 0.1M NaOH or 0.1M HCl if necessary.

TABLE 3

Biofim Kill results versus Total HSP value
(20% solvent, 1% active Sodium
Laureth Sulfate [SLES] as surfactant).

| Solvent | Total HSP | Avg. Log RLU +/− 95% CI |
|---|---|---|
| 1,3 propanediol | 31.7 | 6.56 |
| propylene glycol | 30.2 | 6.60 |
| 2,3 butanediol | 29.8 | 6.35 |
| 1,4 butanediol | 28.9 | 6.67 |
| 1,3 butanediol | 27.8 | 6.63 |
| 2 methyl 1,3 propanediol | 27.7 | 6.56 |
| 2 methyl 2,4 pentanediol | 27.5 | 5.40 |
| 1,2 butanediol | 26.7 | 5.26 |
| 2,2 dimethyl 1,3 propanediol | 26.6 | 5.31 |

Example 2

The efficacy of biofilm kill with 0.25% Poloxamer 407 surfactant in an in-vitro single species *S. mutans* biofilm model.

The six tested formulations included:
0.0323% Menthol USP (essential oil)
0.0639% Thymol NF (essential oil)
0.0922% Eucalyptol USP (essential oil)
0.0660% Methyl Salicylate NF (essential oil)
0.0850% Mint Flavor N & A (flavor/essential oil)
20% Sorbitol Solution USP (70%) (sugar alcohol)
0.1170% Saccharin Sodium USP Granular (sweetener)
0.1200% Benzoic Acid USP (pH adjustment)
0.0354% Sodium Benzoate (pH adjustment)
q.s. water
0.25% Poloxamer 407 (non-ionic surfactant), and
20% solvent.

Mouth rinse formulations described above were prepared and tested using an in vitro single-species *S. mutans* biofilm model. A 22-hour *S. mutans* biofilm was grown (N=24) and exposed to the formulation for thirty seconds. After treatment, the biofilm was neutralized and rinsed. The biofilm was harvested via sonication using a Misonix XL-2000 Ultrasonic processor (Qsonica, LLC, Newtown, Conn.). Using a Celsis Rapid Detection RapiScreen kit (Celsis International PLC, Chicago). The bacteria was lysed with Celsis Luminex and then the adenosine triphosphate (ATP) from the bacteria was measured using the bioluminescence marker Celsis LuminATE. ATP concentration was measured by RLUs (relative light units) which is an indication of cell viability. Decreasing log RLUs indicates fewer bacteria alive after treatment. Decreasing log RLUs Sterile water negative controls usually yield a log RLU of between 7.0 and 8.0, while the positive control (a commercially available essential oil mouth rinse) usually yield a log RLU of between 5.5 and 6.5.

Table 4 shows the in-vitro single species *S. mutans* biofilm model kill results with respect to the total Hansen Solubility Parameter (HSP) value for the six formulations with 20% solvent loading and 0.25% Poloxamer 407 surfactant. Final formulations were adjusted to pH 4.2 with 0.1M NaOH or 0.1M HCl if necessary.

TABLE 4

Biofim Kill results versus Total HSP value
(20% solvent, 0.25% Poloxamer 407 as surfactant).

| Solvent | Total HSP | Avg. Log RLU +/− 95% CI |
|---|---|---|
| 1,3 propanediol | 31.7 | 7.40 |
| propylene glycol | 30.2 | 7.09 |
| 1,3 butanediol | 27.8 | 7.36 |
| 2 methyl 2,4 pentanediol | 27.5 | 5.7 |
| 1,2 butanediol | 26.7 | 6.58 |
| 2,2 dimethyl 1,3 propanediol | 26.6 | 6.47 |

Example 3

The efficacy of biofilm kill with 20% 1,2 butanediol solvent and various surfactants in an in-vitro single species *S. mutans* biofilm model.

The four tested formulations included:
0.0323% Menthol USP (essential oil)
0.0639% Thymol NF (essential oil)
0.0922% Eucalyptol USP (essential oil)
0.0660% Methyl Salicylate NF (essential oil)
0.0850% Mint Flavor N & A (flavor/essential oil)
20% Sorbitol Solution USP (70%) (sugar alcohol)
0.1170% Saccharin Sodium USP Granular (sweetener)
0.1200% Benzoic Acid USP (pH adjustment)
0.0354% Sodium Benzoate (pH adjustment)
q.s. water
X % surfactant, and
20% 1,2 butanediol.

Mouth rinse formulations described above were prepared and tested using an in vitro single-species *S. mutans* biofilm model. A 22-hour *S. mutans* biofilm was grown (N=24) and exposed to the formulation for thirty seconds. After treatment, the biofilm was neutralized and rinsed. The biofilm was harvested via sonication using a Misonix XL-2000 Ultrasonic processor (Qsonica, LLC, Newtown, Conn.). Using a Celsis Rapid Detection RapiScreen kit (Celsis International PLC, Chicago). The bacteria was lysed with Celsis Luminex and then the adenosine triphosphate (ATP) from the bacteria was measured using the bioluminescence marker Celsis LuminATE. ATP concentration was measured by RLUs (relative light units) which is an indication of cell viability. Decreasing log RLUs indicates fewer bacteria alive after treatment. Decreasing log RLUs Sterile water negative controls usually yield a log RLU of between 7.0 and 8.0, while the positive control (a commercially available essential oil mouth rinse) usually yield a log RLU of between 5.5 and 6.5.

Table 5 shows the in-vitro single species *S. mutans* biofilm model kill results with respect to different surfactants for the four formulations with 20% 1,2 butanediol solvent loading. Final formulations were adjusted to pH 4.2 with 0.1M NaOH or 0.1M HCl if necessary.

TABLE 5

Biofim Kill results versus surfactant
(20% 1,2 butanediol as solvent).

| Surfactant | Avg. Log RLU +/− 95% Cl |
|---|---|
| 0.35% sodium methyl cocoyl taurate | 4.38 |
| 0.4% sodium lauroyl sarcosinate | 4.39 |
| 0.25% cocoamdiopropyl betaine | 4.75 |
| 0.5% sucrose laurate | 4.79 |

Table 5 shows all of the surfactants have sufficient biofilm efficacy when used with 1,2 butanediol as a solvent.

Example 4

The efficacy of biofilm kill with 1% active Sodium Laureth Sulfate surfactant in an in-vitro single species *S. mutans* biofilm model.

The tested formulation included:
0.0323% Menthol USP (essential oil)
0.0639% Thymol NF (essential oil)
0.0922% Eucalyptol USP (essential oil)
0.0660% Methyl Salicylate NF (essential oil)
0.0850% Mint Flavor N & A (flavor/essential oil)
20% Sorbitol Solution USP (70%) (sugar alcohol)
0.1170% Saccharin Sodium USP Granular (sweetener)
0.1200% Benzoic Acid USP (pH adjustment)
0.0354% Sodium Benzoate (pH adjustment)
q.s. water
1% active Sodium Laureth Sulfate (non-ionic surfactant), and
15% 1,2 butanediol.

Mouth rinse formulations described above were prepared and tested using an in vitro single-species *S. mutans* biofilm model. A 22-hour *S. mutans* biofilm was grown (N=24) and exposed to the formulation for thirty seconds. After treatment, the biofilm was neutralized and rinsed. The biofilm was harvested via sonication using a Misonix XL-2000 Ultrasonic processor (Qsonica, LLC, Newtown, Conn.). Using a Celsis Rapid Detection RapiScreen kit (Celsis International PLC, Chicago). The bacteria was lysed with Celsis Luminex and then the adenosine triphosphate (ATP) from the bacteria was measured using the bioluminescence marker Celsis LuminATE. ATP concentration was measured by RLUs (relative light units) which is an indication of cell viability. Decreasing log RLUs indicates fewer bacteria alive after treatment. Decreasing log RLUs Sterile water negative controls usually yield a log RLU of between 7.0 and 8.0, while the positive control (a commercially available essential oil mouth rinse) usually yield a log RLU of between 5.5 and 6.5.

The resulting Avg. Log RLU+/−95% Cl for the formulation was 5.31.

Example 5

The efficacy of biofilm kill with differential concentration of 1,3 butanediol, sorbitol, and 0.25% Poloxamer 407 surfactant in an in-vitro single species *S. mutans* biofilm model.

The four tested formulations included:
0.0323% Menthol USP (essential oil)
0.0639% Thymol NF (essential oil)
0.0922% Eucalyptol USP (essential oil)
0.0660% Methyl Salicylate NF (essential oil)
0.0850% Mint Flavor N & A (flavor/essential oil)
10-30% Sorbitol Solution USP (70%) (sugar alcohol)
0.1170% Saccharin Sodium USP Granular (sweetener)
0.0500% Sucralose NF (sweetener)
0.1200% Benzoic Acid USP (pH adjustment)
0.0354% Sodium Benzoate (pH adjustment)
0.0050% FD&C Green No. 3
q.s. water
0.25% Poloxamer 407 (non-ionic surfactant), and
5-20% 1,3 butanediol.

Mouth rinse formulations described above were prepared and tested using an in vitro single-species *S. mutans* biofilm model. A 22-hour *S. mutans* biofilm was grown (N=24) and exposed to the formulation for thirty seconds. After treatment, the biofilm was neutralized and rinsed. The biofilm was harvested via sonication using a Misonix XL-2000 Ultrasonic processor (Qsonica, LLC, Newtown, Conn.). Using a Celsis Rapid Detection RapiScreen kit (Celsis International PLC, Chicago). The bacteria was lysed with Celsis Luminex and then the adenosine triphosphate (ATP) from the bacteria was measured using the bioluminescence marker Celsis LuminATE. ATP concentration was measured by RLUs (relative light units) which is an indication of cell viability. Decreasing log RLUs indicates fewer bacteria alive after treatment.

Table 6 shows results of the *S. mutans* biofilm kill tests, in log RLU, for formulations with 5% and 20% solvent loading and 0.25 wt % Poloxamer 407 surfactant. Final formulations were adjusted to pH 4.2 with 0.1M NaOH or 0.1M HCl if necessary.

TABLE 6

Biofilm Kill results versus varying solvent
and sorbitol levels (5-20% solvent, 10-30%
sorbitol, 0.25% Poloxamer 407 as surfactant).

| Solvent | Total HSP | 1,3 butanediol (%) | Sorbitol (%) | Avg. Log RLU +/− 95% Cl |
|---|---|---|---|---|
| 1,3 butanediol | 27.8 | 5 | 10 | 5.63 |
| 1,3 butanediol | 27.8 | 20 | 10 | 6.35 |
| 1,3 butanediol | 27.8 | 5 | 30 | 5.68 |
| 1,3 butanediol | 27.8 | 20 | 30 | 5.83 |

Example 6

The efficacy of biofilm kill with 1% active Sodium Laureth Sulfate surfactant in an in-vitro single species *S. mutans* biofilm model.

The tested formulation included:
0.0323% Menthol USP (essential oil)
0.0639% Thymol NF (essential oil)
0.0922% Eucalyptol USP (essential oil)
0.0660% Methyl Salicylate NF (essential oil)
0.0850% Mint Flavor N & A (flavor/essential oil)
20% Sorbitol Solution USP (70%) (sugar alcohol)
0.1170% Saccharin Sodium USP Granular (sweetener)
0.1200% Benzoic Acid USP (pH adjustment)
0.0354% Sodium Benzoate (pH adjustment)
q.s. water
1% active Sodium Laureth Sulfate (non-ionic surfactant), and
5% 1,2 butanediol.

Mouth rinse formulations described above were prepared and tested using an in vitro single-species *S. mutans* biofilm model. A 22-hour *S. mutans* biofilm was grown (N=24) and exposed to the formulation for thirty seconds. After treatment, the biofilm was neutralized and rinsed. The biofilm was harvested via sonication using a Misonix XL-2000 Ultrasonic processor (Qsonica, LLC, Newtown, Conn.). Using a Celsis Rapid Detection RapiScreen kit (Celsis International PLC, Chicago). The bacteria was lysed with Celsis Luminex and then the adenosine triphosphate (ATP) from the bacteria was measured using the bioluminescence marker Celsis LuminATE. ATP concentration was measured by RLUs (relative light units) which is an indication of cell viability. Decreasing log RLUs indicates fewer bacteria alive after treatment. Decreasing log RLUs Sterile water negative controls usually yield a log RLU of between 7.0 and 8.0, while the positive control (a commercially available essential oil mouth rinse) usually yield a log RLU of between 5.5 and 6.5.

The resulting Avg. Log RLU+/−95% Cl for the formulation was 6.55.

Example 7

The efficacy of biofilm kill with 1% active Sodium Laureth Sulfate surfactant in an in-vitro single species *S. mutans* biofilm model.

The tested formulation included:
0.0323% Menthol USP (essential oil)
0.0639% Thymol NF (essential oil)
0.0922% Eucalyptol USP (essential oil)
0.0660% Methyl Salicylate NF (essential oil)
0.0850% Mint Flavor N & A (flavor/essential oil)
20% Sorbitol Solution USP (70%) (sugar alcohol)
0.1170% Saccharin Sodium USP Granular (sweetener)
0.1200% Benzoic Acid USP (pH adjustment)
0.0354% Sodium Benzoate (pH adjustment)
q.s. water
1% active Sodium Laureth Sulfate (non-ionic surfactant), and
10% 1,2 butanediol.

Mouth rinse formulations described above were prepared and tested using an in vitro single-species *S. mutans* biofilm model. A 22-hour *S. mutans* biofilm was grown (N=24) and exposed to the formulation for thirty seconds. After treatment, the biofilm was neutralized and rinsed. The biofilm was harvested via sonication using a Misonix XL-2000 Ultrasonic processor (Qsonica, LLC, Newtown, Conn.). Using a Celsis Rapid Detection RapiScreen kit (Celsis International PLC, Chicago). The bacteria was lysed with Celsis Luminex and then the adenosine triphosphate (ATP) from the bacteria was measured using the bioluminescence marker Celsis LuminATE. ATP concentration was measured by RLUs (relative light units) which is an indication of cell viability. Decreasing log RLUs indicates fewer bacteria alive after treatment. Decreasing log RLUs Sterile water negative controls usually yield a log RLU of between 7.0 and 8.0, while the positive control (a commercially available essential oil mouth rinse) usually yield a log RLU of between 5.5 and 6.5.

The resulting Avg. Log RLU+/−95% Cl for the formulation was 6.23.

Example 8

The efficacy of biofilm kill with 1% active Sodium Laureth Sulfate surfactant in an in-vitro single species *S. mutans* biofilm model.

The tested formulation included:
0.0323% Menthol USP (essential oil)
0.0639% Thymol NF (essential oil)
0.0922% Eucalyptol USP (essential oil)
0.0660% Methyl Salicylate NF (essential oil)
0.0850% Mint Flavor N & A (flavor/essential oil)
20% Sorbitol Solution USP (70%) (sugar alcohol)
0.1170% Saccharin Sodium USP Granular (sweetener)
0.1200% Benzoic Acid USP (pH adjustment)
0.0354% Sodium Benzoate (pH adjustment)
q.s. water
1% active Sodium Laureth Sulfate (non-ionic surfactant), and
15% 1,2 butanediol.

Mouth rinse formulations described above were prepared and tested using an in vitro single-species *S. mutans* biofilm model. A 22-hour *S. mutans* biofilm was grown (N=24) and exposed to the formulation for thirty seconds. After treatment, the biofilm was neutralized and rinsed. The biofilm was harvested via sonication using a Misonix XL-2000 Ultrasonic processor (Qsonica, LLC, Newtown, Conn.). Using a Celsis Rapid Detection RapiScreen kit (Celsis International PLC, Chicago). The bacteria was lysed with Celsis Luminex and then the adenosine triphosphate (ATP) from the bacteria was measured using the bioluminescence marker Celsis LuminATE. ATP concentration was measured by RLUs (relative light units) which is an indication of cell viability. Decreasing log RLUs indicates fewer bacteria alive after treatment. Decreasing log RLUs Sterile water negative controls usually yield a log RLU of between 7.0 and 8.0, while the positive control (a commercially available essential oil mouth rinse) usually yield a log RLU of between 5.5 and 6.5.

The resulting Avg. Log RLU+/−95% Cl for the formulation was 5.90.

Example 9

The efficacy of biofilm kill with 1% active Sodium Laureth Sulfate surfactant in an in-vitro single species *S. mutans* biofilm model.

The tested formulation included:
0.0323% Menthol USP (essential oil)
0.0639% Thymol NF (essential oil)
0.0922% Eucalyptol USP (essential oil)
0.0660% Methyl Salicylate NF (essential oil)
0.0850% Mint Flavor N & A (flavor/essential oil)
10% Sorbitol Solution USP (70%) (sugar alcohol)
0.1170% Saccharin Sodium USP Granular (sweetener)
0.1200% Benzoic Acid USP (pH adjustment)
0.0354% Sodium Benzoate (pH adjustment)
q.s. water 0.25% Poloxamer 407 (non-ionic surfactant), and
20% solvent.

Mouth rinse formulations described above were prepared and tested using an in vitro single-species *S. mutans* biofilm model. A 22-hour *S. mutans* biofilm was grown (N=24) and exposed to the formulation for thirty seconds. After treatment, the biofilm was neutralized and rinsed. The biofilm was harvested via sonication using a Misonix XL-2000 Ultrasonic processor (Qsonica, LLC, Newtown, Conn.). Using a Celsis Rapid Detection RapiScreen kit (Celsis International PLC, Chicago). The bacteria was lysed with Celsis Luminex and then the adenosine triphosphate (ATP) from the bacteria was measured using the bioluminescence marker Celsis LuminATE. ATP concentration was measured by RLUs (relative light units) which is an indication of cell viability. Decreasing log RLUs indicates fewer bacteria alive after treatment. Decreasing log RLUs Sterile water negative controls usually yield a log RLU of between 7.0 and 8.0, while the positive control (a commercially available essential oil mouth rinse) usually yield a log RLU of between 5.5 and 6.5.

The resulting Avg. Log RLU+/−95% Cl for the formulation was 4.83.

Example 10

The efficacy of biofilm kill with 1% active Sodium Laureth Sulfate surfactant in an in-vitro single species *S. mutans* biofilm model.

The tested formulation included:
0.0323% Menthol USP (essential oil)
0.0639% Thymol NF (essential oil)
0.0922% Eucalyptol USP (essential oil)
0.0660% Methyl Salicylate NF (essential oil)
0.0850% Mint Flavor N & A (flavor/essential oil)
14% Xylitol Solution (sugar alcohol)
0.1170% Saccharin Sodium USP Granular (sweetener)
0.1200% Benzoic Acid USP (pH adjustment)
0.0354% Sodium Benzoate (pH adjustment)
q.s. water
0.25% Poloxamer 407 (non-ionic surfactant), and
10% 1,2 butanediol.

Mouth rinse formulations described above were prepared and tested using an in vitro single-species *S. mutans* biofilm model. A 22-hour *S. mutans* biofilm was grown (N=24) and exposed to the formulation for thirty seconds. After treatment, the biofilm was neutralized and rinsed. The biofilm was harvested via sonication using a Misonix XL-2000 Ultrasonic processor (Qsonica, LLC, Newtown, Conn.). Using a Celsis Rapid Detection RapiScreen kit (Celsis International PLC, Chicago). The bacteria was lysed with Celsis Luminex and then the adenosine triphosphate (ATP) from the bacteria was measured using the bioluminescence marker Celsis LuminATE. ATP concentration was measured by RLUs (relative light units) which is an indication of cell viability. Decreasing log RLUs indicates fewer bacteria alive after treatment. Decreasing log RLUs Sterile water negative controls usually yield a log RLU of between 7.0 and 8.0, while the positive control (a commercially available essential oil mouth rinse) usually yield a log RLU of between 5.5 and 6.5.

The resulting Avg. Log RLU+/−95% Cl for the formulation was 4.82.

Example 11

The efficacy of biofilm kill with 1% active Sodium Laureth Sulfate surfactant in an in-vitro single species *S. mutans* biofilm model.

The four tested formulations included:
0.0323% Menthol USP (essential oil)
0.0639% Thymol NF (essential oil)
0.0922% Eucalyptol USP (essential oil)
0.0660% Methyl Salicylate NF (essential oil)
0.0850% Mint Flavor N & A (flavor/essential oil)
0.1170% Saccharin Sodium USP Granular (sweetener)
0.1200% Benzoic Acid USP (pH adjustment)
0.0354% Sodium Benzoate (pH adjustment)
q.s. water
1% active Sodium Laureth Sulfate (non-ionic surfactant), and
5-25%% solvent.

Mouth rinse formulations described above were prepared and tested using an in vitro single-species *S. mutans* biofilm model. A 22-hour *S. mutans* biofilm was grown (N=24) and exposed to the formulation for thirty seconds. After treatment, the biofilm was neutralized and rinsed. The biofilm was harvested via sonication using a Misonix XL-2000 Ultrasonic processor (Qsonica, LLC, Newtown, Conn.). Using a Celsis Rapid Detection RapiScreen kit (Celsis International PLC, Chicago). The bacteria was lysed with Celsis Luminex and then the adenosine triphosphate (ATP) from the bacteria was measured using the bioluminescence marker Celsis LuminATE. ATP concentration was measured by RLUs (relative light units) which is an indication of cell viability. Decreasing log RLUs indicates fewer bacteria alive after treatment. Decreasing log RLUs Sterile water negative controls usually yield a log RLU of between 7.0 and 8.0, while the positive control (a commercially available essential oil mouth rinse) usually yield a log RLU of between 5.5 and 6.5.

TABLE 7

Biofilm Kill results versus varying solvent levels (5-25% solvent, 1% active Sodium Laureth Sulfate [SLES] as surfactant).

| Solvent | Total HSP | 1,2 butanediol (%) | Avg. Log RLU +/− 95% Cl |
|---|---|---|---|
| 1,2 butanediol | 26.7 | 5 | 6.08 |
| 1,2 butanediol | 26.7 | 15 | 5.54 |
| 1,2 butanediol | 26.7 | 20 | 5.26 |
| 1,2 butanediol | 26.7 | 25 | 4.96 |

Example 12

The efficacy of biofilm kill with 1% active Sodium Laureth Sulfate surfactant in an in-vitro single species *S. mutans* biofilm model.

The five tested formulations included:
0.0323% Menthol USP (essential oil)
0.0639% Thymol NF (essential oil)
0.0922% Eucalyptol USP (essential oil)
0.0660% Methyl Salicylate NF (essential oil)
0.0850% Mint Flavor N & A (flavor/essential oil)
0.1170% Saccharin Sodium USP Granular (sweetener)
0.1200% Benzoic Acid USP (pH adjustment)
0.0354% Sodium Benzoate (pH adjustment)
q.s. water
1% active Sodium Laureth Sulfate (non-ionic surfactant), and
5-25% solvent.

Mouth rinse formulations described above were prepared and tested using an in vitro single-species *S. mutans* biofilm model. A 22-hour *S. mutans* biofilm was grown (N=24) and exposed to the formulation for thirty seconds. After treatment, the biofilm was neutralized and rinsed. The biofilm was harvested via sonication using a Misonix XL-2000 Ultrasonic processor (Qsonica, LLC, Newtown, Conn.). Using a Celsis Rapid Detection RapiScreen kit (Celsis International PLC, Chicago). The bacteria was lysed with Celsis Luminex and then the adenosine triphosphate (ATP) from the bacteria was measured using the bioluminescence marker Celsis LuminATE. ATP concentration was measured by RLUs (relative light units) which is an indication of cell viability. Decreasing log RLUs indicates fewer bacteria alive after treatment. Decreasing log RLUs Sterile water negative controls usually yield a log RLU of between 7.0 and 8.0, while the positive control (a commercially available essential oil mouth rinse) usually yield a log RLU of between 5.5 and 6.5.

TABLE 8

Biofilm Kill results versus varying solvent levels (5-25% solvent, 1% active Sodium Laureth Sulfate [SLES] as surfactant).

| Solvent | Total HSP | 2 methyl 2,4 pentanediol (%) | Avg. Log RLU +/− 95% CI |
| --- | --- | --- | --- |
| 2 methyl 2,4 pentanediol | 27.5 | 5 | 5.73 |
| 2 methyl 2,4 pentanediol | 27.5 | 10 | 5.56 |
| 2 methyl 2,4 pentanediol | 27.5 | 15 | 5.51 |
| 2 methyl 2,4 pentanediol | 27.5 | 20 | 5.40 |
| 2 methyl 2,4 pentanediol | 27.5 | 25 | 5.37 |

What is claimed is:

1. An oral care composition comprising one or more polyol solvents having a total Hansen Solubility Parameter (HSP) of from about 25 to 27.5, one or more non-anionic bioactive agents, and an aqueous phase, wherein the oral care composition is essentially free of alkyl sulfate surfactants.

2. The composition of claim 1 wherein said one or more polyol solvents are selected from the group consisting of 2-methyl-2,4-pentanediol, 1,2-butanediol, 2,2-dimethyl-1,3-propanediol, and mixtures of two or more thereof.

3. The composition of claim 1 wherein said one or more non-anionic bioactive agents are selected from the group consisting of thymol, eucalyptol, menthol, methyl salicylate, and combinations of two or more thereof.

4. The composition of claim 1 wherein said composition is free of alkyl sulfate surfactants.

5. The composition of claim 1 further comprising at least one alkyl ether sulfate.

6. The composition of claim 5 wherein said at least one alkyl ether sulfate comprises sodium laureth sulfate.

7. The composition of claim 1 further comprising at least one poloxamer surfactant.

8. The composition of claim 7 wherein said at least one poloxamer surfactant is selected from the group consisting of poloxamer 407, poloxamer 188, poloxamer 108, and combinations of two or more thereof.

9. The composition of claim 1 having an amount of $C_2$-$C_4$ monohydric alcohol up to about 1.0% v/v4.

10. The composition of claim 1 further comprising sugar alcohol in an amount of from about 7% to about 30% w/v.

11. The composition of claim 10 wherein said sugar alcohol comprises sorbitol.

12. An oral care composition comprising one or more polyol solvents selected from the group consisting of 2-methyl-2,4-pentanediol, 1,2-butanediol, 2,2-dimethyl-1,3-propanediol, and mixtures of two or more thereof; one or more non-anionic bioactive agents selected from the group consisting of thymol, eucalyptol, menthol, methyl salicylate, and combinations of two or more thereof; sorbitol; and water, wherein the oral care composition is essentially free of alkyl sulfate surfactants.

13. The oral care composition of claim 12 further comprising a surfactant selected from the group consisting of sodium laureth sulfate, poloxamer 407, poloxamer 188, and combinations of two or more thereof.

14. The oral care composition of claim 13 wherein said surfactant comprises poloxamer 407.

15. The composition of claim 13 wherein said composition is free of alkyl sulfate surfactants.

16. The composition of claim 15 having an amount of $C_2$-$C_4$ monohydric alcohol of about 1.0% v/v or less.

17. The composition of claim 13 comprising a total weight of from about 5% to about 30% by weight of said one or more polyol solvents, from about 0.001 to about 0.35% w/v of said one or more non-anionic bioactive agents; and from about 7% to about 30% w/v of said sorbitol.

18. A method of reducing the number of oral microorganisms responsible for one or more conditions selected from the group consisting of plaque, gingivitis, gum disease, oral malodor and combinations of two or more of such conditions in the oral cavity, said method comprising the step of applying a composition of claim 1 to a surface of the oral cavity.

19. A method of reducing the number of oral microorganisms responsible for one or more conditions selected from the group consisting of plaque, gingivitis, gum disease, oral malodor and combinations of two or more of such conditions in the oral cavity, said method comprising the step of applying a composition of claim 12 to a surface of the oral cavity.

* * * * *